(12) United States Patent
Garnier et al.

(10) Patent No.: US 6,368,584 B1
(45) Date of Patent: Apr. 9, 2002

(54) DETERGENT COSMETIC COMPOSITIONS COMPRISING AN ANIONIC HYDROXYALKYL ETHER SURFACTANT AND A SILICONE, AND THEIR USES

(75) Inventors: Nathalie Garnier, Springfield, NJ (US); Danièle Cauwet-Martin, Paris; Serge Restle, Saint-Prix, both of (FR)

(73) Assignee: L'Oreal S.A., Paris (FR)

(*) Notice: Subject to any disclaimer, the term of this patent is extended or adjusted under 35 U.S.C. 154(b) by 0 days.

(21) Appl. No.: 09/504,376

(22) Filed: Feb. 15, 2000

(51) Int. Cl.[7] .................... A61K 7/08; A61K 7/075
(52) U.S. Cl. ............ 424/70.22; 424/70.1; 424/70.11; 424/70.12; 424/70.121; 424/70.122; 424/70.19; 424/70.21; 424/70.27; 424/70.31; 510/119
(58) Field of Search .................... 424/70.1, 70.11, 424/70.12, 70.121, 70.122, 70.19, 70.21, 70.22, 70.27, 70.31; 510/119

(56) References Cited

U.S. PATENT DOCUMENTS

| | | | |
|---|---|---|---|
| 2,528,378 A | | 10/1950 | Mannheimer |
| 2,781,354 A | | 2/1957 | Mannheimer |
| 4,591,610 A | * | 5/1986 | Grollier |
| 4,693,935 A | | 9/1987 | Mazurek |
| 4,728,571 A | | 3/1988 | Clemens et al. |
| 4,972,037 A | | 11/1990 | Garbe et al. |
| 5,476,649 A | * | 12/1995 | Naito et al. |
| 5,490,955 A | | 2/1996 | Hagan et al. |
| 5,756,080 A | * | 5/1998 | Janchitraponvej et al. |

FOREIGN PATENT DOCUMENTS

| | | | |
|---|---|---|---|
| EP | 0 185 507 | | 6/1986 |
| EP | 0 291 207 | | 11/1988 |
| EP | 0 337 354 | | 10/1989 |
| EP | 0 342 834 | | 11/1989 |
| EP | 0 412 704 | | 2/1991 |
| EP | 0 412 707 | | 2/1991 |
| EP | 0 492 657 | | 7/1992 |
| EP | 0 582 152 | | 2/1994 |
| EP | 0 864 638 | | 9/1998 |
| FR | 2 270 846 | | 12/1975 |
| FR | 2 383 660 | | 10/1978 |
| FR | 2 470 596 | | 6/1981 |
| FR | 2 519 863 | | 7/1983 |
| FR | 2 598 611 | | 11/1987 |
| JP | 57-162797 | | 10/1982 |
| JP | 62-149797 | | 7/1987 |
| JP | 63-280008 | * | 11/1988 |
| JP | 63-280798 | | 11/1988 |
| JP | 4-122797 | | 4/1992 |
| JP | 4-122799 | | 4/1992 |
| JP | 5-92914 | | 4/1993 |
| JP | 6-316546 | | 11/1994 |
| JP | 7-304652 | | 11/1995 |
| JP | 7-304653 | * | 11/1995 |
| JP | 8-3101 | | 1/1996 |
| JP | 8-269482 | | 10/1996 |
| JP | 8-269487 | * | 10/1996 |
| JP | 8-269489 | * | 10/1996 |
| JP | 11-269488 | * | 10/1999 |
| WO | WO 39/23009 | | 11/1993 |
| WO | WO 93/23446 | | 11/1993 |
| WO | WO 94/17783 | | 8/1994 |
| WO | WO 95/00578 | | 1/1995 |
| WO | WO 95/03776 | | 2/1995 |
| WO | WO 98/00486 | | 1/1998 |

OTHER PUBLICATIONS

Uehara et al., Composition of Preparation For External Application to The Skin, Nov. 17, 1988 (translation of Japanese Patent 63–280008).*
Richard J. Lewis, Sr., Hawley's Condensed Chemical Dictionary (John Wiley & Sons, Inc. 1997).*
Charles Zviak, The Science of Hair Care (Marcel Dekker, Inc. 1986).*
English language Derwent Abstract of JP 62–149797.
English language Derwent Abstract of JP 57–162797.
English language Derwent Abstract of JP 63–280008.
English language Derwent Abstract of JP 4–122797.
English language Derwent Abstract of JP 4–122799.
English language Derwent Abstract of JP 5–92914.
English language Derwent Abstract of JP 6–316546.
English language Derwent Abstract of JP 7–304652.
English language Derwent Abstract of JP 7–304653.
English language Derwent Abstract of JP 8–3101.
English language Derwent Abstract of JP 8–269487.
English language Derwent Abstract of JP 8–269489.
Amihud Karmer, "Revised Tables for Determining Significance of Differences", Food Technology, vol. 17, No. 12, Dec. 1963, pp. 124–125.

(List continued on next page.)

Primary Examiner—Thurman K. Page
Assistant Examiner—Brian K. Seidleck
(74) Attorney, Agent, or Firm—Finnegan, Henderson, Farabow, Garrett & Dunner, L.L.P.

(57) ABSTRACT

The invention relates to novel detergent cosmetic compositions comprising, in a cosmetically acceptable medium, at least one anionic surfactant chosen from 2-hydroxyalkyl ether carboxylic acid and salts thereof and at least one silicone chosen from: (i) volatile or non-volatile, linear, branched or cyclic and crosslinked or non-crosslinked polyalkylsiloxanes, polyarylsiloxanes or polyalkylarylsiloxanes; (ii) polysiloxanes comprising, in their general structure, one or more organofunctional groups chosen from: a) substituted or unsubstituted aminated groups; b) (per)fluorinated groups; c) thiol groups; d) carboxylate groups; e) hydroxylated groups; f) alkoxylated groups; g) acyloxyalkyl groups; h) amphoteric groups; i) bisulphite groups; j) hydroxyacylamino groups; k) carboxylic acid groups; l) sulphonic groups; m) sulphate or thiosulphate groups; (iii) linear polysiloxane(A)-polyoxyalkylene(B) block copolymers of (A—B)$_n$ type with n>3; (iv) grafted silicone polymers composed of a main chain not comprising silicone; and (v) grafted silicone polymers composed of a polysiloxane main chain.

29 Claims, No Drawings

OTHER PUBLICATIONS

M.R. Porter, "Handbook of Surfactants", Blackie & Sons Ltd., Glasgow & London, 1991, pp. 116–178.
Charles Todd, "Volatile Silicone Fluids for Cosmetic Formulations", Cosmetics and Toiletries, vol. 91, Jan. 1976, pp. 29–32.
English language Derwent Abstract of FR 2 270 846.
English language Derwent Abstract of FR 2 383 660.
English language abstract of FR 2 470 596.
English language abstract of FR 2 519 863.
English language Derwent Abstract of FR 2 598 611.
English language Derwent Abstract of JP 63–280798.
English language Derwent Abstract of JP 8–269482.

* cited by examiner

DETERGENT COSMETIC COMPOSITIONS COMPRISING AN ANIONIC HYDROXYALKYL ETHER SURFACTANT AND A SILICONE, AND THEIR USES

The present invention relates to novel cosmetic compositions comprising, in a cosmetically acceptable medium, at least one hydroxyalkyl ether carboxylic anionic surfactant and at least on silicone.

Detergent compositions (shampoo or shower gel) based essentially on conventional surface-active agent of, in particular, anionic, non-ionic and/or amphoteric type, but more particularly of anionic type, are commonly used for cleaning and/or washing the hair and/or the skin. These compositions are applied to wet hair or skin and the foam generated by massaging or rubbing with the hands makes it possible, after rinsing with water, to remove the various types of dirt initially present on the hair or skin.

These base compositions certainly have a good washing power but the intrinsic cosmetic properties which are attached to them remain fairly weak, however, because the relatively aggressive nature of such a cleaning treatment can, in the long term, result in more or less marked damage to keratinous substances, related to the gradual removal of the lipids or proteins present in or at the surface of the keratinous su stances.

Consequently, in order to improve the cosmetic properties of the above detergent compositions and more particularly of those which are intended to be applied to sensitized hair (i.e. hair which is found to be damaged or embrittled, in particular under the chemical action of atmospheric agents and/or of hair treatments, such as permings, dyeings or bleachings), it is now usual to introduce into the latter additional cosmetic agents, known as conditioning agents, intended mainly to repair or limit the harmful or undesirable effects brought about by the various treatments or attacks to which the hair fibres are more or less repeatedly subjected. These conditioning agents can, of course, also improve the cosmetic behaviour of natural hair.

Currently, the most widely used conditioning agents in shampoos are cationic polymers, silicones and/or silicone derivatives, this being because these confer, on dry or wet washed hair, an ease of disentangling, a softness and a sleekness which are increased with respect to the which can be obtained with the corresponding cleaning compositions which are devoid thereof.

However, and in spite of the progress achieved recently in the field of shampoos based on cationic polymers and/or on silicone, the latter are not really completely satisfactory, so that strong need still currently exists with regard to being able to have available novel products exhibiting a better performance with regard to one or more of the cosmetic properties mentioned above.

Anionic surfactants of hydroxyalkyl ether carboxylic type have already been recommended in detergent cosmetic compositions. They have been disclosed, for example, in Patent Applications J63280798, J08268487 and J08269482, all of which are incorporated herein by reference.

Hair washing composition using these surfactants alone do not result in satisfactory cosmetic properties.

The aim of the invention is therefore to provide detergent cosmetic compositions exhibiting improved cosmetic properties, in particular hair disentangling, sleekness and softness. In point of fact, it has now for the first time been found that the combination of specific silicones and of a hydroxyalkyl ether carboxylic anionic surfactant makes it possible to achieve these aims.

These novel compositions make it possible to achieve better deposition of these silicones on keratinous substances (in particular the hair) than a composition comprising conventional anionic surfactants, such as alkyl ether carboxylate salts, this being without a visual appearance or greasy feel.

The compositions according to the invention confer on keratinous substances, in particular the hair, a notable treating effect which is revealed in particular by an ease of disentangling and a contribution of volume, of lightness, of sleekness, of softness and of suppleness and of manageability without any sensation of a feeling of heaviness.

One subject of the invention is thus a detergent cosmetic composition, characterized in that it comprise, in a cosmetically acceptable medium, at least one anionic surfactant chosen from 2-hydroxyalkyl ether carboxylic acid or salts thereof and at least one silicone polymer chosen from:

(i) volatile or non-volatile, linear, branched or cyclic and crosslinked or non-crosslinked polyalkylsiloxanes, polyarylsiloxanes or polyalkylaryisiloxanes, (ii) polysiloxanes comprising, in their general structure, one or more organofunctional groups chosen from:
 a) substituted or unsubstituted aminated groups
 b) (per)fluorinated groups
 c) thiol groups
 d) carboxylate groups
 e) hydroxylated groups
 f) alkoxylated groups
 g) acyloxyalkyl groups
 h) amphoteric groups
 i) bisulphite groups
 j) hydroxyacylamino groups
 k) carboxylic acid groups
 l) sulphonic groups
 m) sulphate or thiosulphate groups;

(iii) linear polysiloxane(A)-polyoxyalkylene(B) block copolymers of $(A-B)_n$ type with n>3;

(iv) grafted silicone polymers with a non-silicone organic backbone, which polymers are composed of a main organic chain formed from organic monomers not comprising silicone, on which chain is grafted, inside the said chain and optionally at one at least of its ends, at least one polysiloxane macromonomer; and (v) grafted silicone polymers with a polysiloxane backbone which is grafted with non-silicone organic monomers, comprising a main polysiloxane chain on which is grafted, inside the said chain and optionally at one at least of its ends, at least one organic macromonomer not comprising silicone.

Another object of the invention relates to a process for the treatment of keratinous substances, such as hair, comprising applying to the said substances, cosmetic compositions according to the invention.

A further object of the invention is the use of a composition according to the invention in disentangling or sleeking the hair or in contributing volume, lightness, softness, suppleness and manageability to the hair.

A further object of the invention is the use of surfactants chosen from 2-hydroxyalkyl ether carboxylic acid or salts thereof in or for the manufacture of detergent cosmetic compositions comprising at least one silicone polymer defined above.

According to the present invention, the term "keratinous substances" comprises the hair, eyelashes, eyebrows, skin, nails, mucous membranes or scalp and more particularly the hair.

The various objects of the invention will now be given in detail. All the meanings and definitions of the compounds used in the present invention given hereinbelow are valid for all the subject-matters of the invention.

The anionic surfactants chosen from 2-hydroxyalkyl ether carboxylic acid and salts thereof can have the following structure:

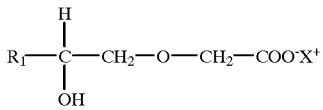

(I)

in which:
- $R^1$ denotes more particularly a saturated or unsaturated, linear or branched alkyl radical comprising from 8 to 30 carbon atoms, and
- X denotes hydrogen or are inorganic or organic cation, such as: those resulting from an alkali metal (for example, $Na^+$ or $K^+$), $NH_4^+$, ammoniums resulting from basic amino acid, such as lysine, arginine, sarcosine, ornithine or citrulline, or ammoniums resulting from aminoalcohols, such as monoethanolamine, diethanolamine, triethanolamine, glucamine, N-methylglucamine or 3-amino-1,2-propanediol.

Preferred 2-hydroxyalkyl ether carboxylic acids or salts thereof according to the present invention are compounds of formula (I) in which $R_1$ denotes more particularly a saturated or unsaturated, linear or branched alkyl radical comprising from 8 to 18 carbon atoms. More preferably, $R_1$ denotes a $C_8$–$C_{18}$ radical derived from coconut oil or a mixture of such radicals.

Mention may be made, among the surfactants of formula (I), of the product sold under the name Beaulight Shaa by the company Sanyo.

According to the invention, the anionic surfactant chosen from 2-hydroxyalkyl ether carboxylic acid and salts thereof can represent from 1% to 30% by weight, preferably from 3% to 15% by weight, with respect to the total weight of the final composition.

The silicone polymers which can be used in accordance with the invention can be soluble or insoluble in water or in the final composition. They can be volatile or non-volatile. The silicone polymers which can be used in accordance with the invention are in particular insoluble in water and can be provided in the form of oils, waxes, resins or gums. Silicones are defined in more detail in the work by Walter Noll, "Chemistry and Technology of Silicones", (1968), Academic Press.

When they are volatile, the polyalkoxysiloxanes, polyarylsiloxanes or polyalkylarylsiloxanes are chosen more particularly from those having a boiling point of between 60° C. and 260° C. and more particularly still from:
  (i) cyclic silicones comprising from 3 to 7 silicon atoms and preferably 4 to 5. They are, for example, octamethylcyclotrasiloxane, sold in particular under the name of "Volatile Silicone 7207" by Union Carbide or "Silbionel® 70045 V 2" by Rhône-Poulenc, decamethylcyclopentasiloxane, sold under the name of "Volatile Silicone 7158" by Union Carbide or "Silbionel 70045 V 5" by Rhône-Poulenc, and their mixtures.

Mention may also be made of cyclocopolymers of the dimethylsiloxanes/methylalkylsiloxane type, such as "Silicone Volatile FZ 3109" sold by the company Union Carbide, with the chemical structure:

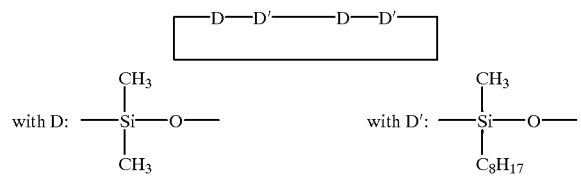

Mention may also be made of mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane ant of 1,1'-oxy(2,2,2',2', 3,3'-hexatrimethylsilyloxy) bisneopentane;

(ii) volatile linear silicones having 2 to 9 silicon atoms and having a viscosity of less than or equal to $5\times10^{6-}$ $m^2/s$ at 25° C. It is, for example, decamethyltetra-siloxane, sold in particular under the name "SH 200" by the company Toray Silicone. Silicones coming within this category are also disclosed in the article published in Cosmetics and Toiletries, Vol. 91, January 76, p. 27–32, Todd & Byers, "Volatile Silicone Fluids for Cosmetics".

In one embodiment of the invention, use is made of non-volatile polyalkylsiloxanes, polyarylsiloxanes or polyalkylarylsiloxanes in the form of oils, of silicone gums or of silicone resins.

Mention may mainly be made, among polyalkylsiloxanes, of:
  linear polydimethylsiloxanes with end trimethylsilyl groups, such as, for example and without implied limitation, Silbione® oils of the 70047 series which are sold by Rhône-Poulenc, Silbione® 47 V 500 000 oil from Rhône-Poulenc, or certain Viscasil products from General Electric;
  linear polydimethylsiloxanes with end hydroxydimethylsilyl groups, such as the oils of the 48 V series from Rhône-Poulenc.

Mention may also be made, in this category of polyalkylsiloxanes, of the polyalkylsiloxanes sold by the company Goldschmidt under the trade names Abilwax® 9800 and Abilwax® 9801, which are poly($C_1$–$C_{20}$) alkylsiloxanes.

The polyalkylsiloxanes preferably have a viscosity of greater than or equal to 500 cSt (5 $cm^2/s$). The viscosity of the silicones is measured at 25° C. according to ASTM Standard 445, Appendix C.

Mention may be made, among polyalkylarylsiloxanes, of linear or branched polydimethylmethylphenylsiloxanes or polydimethyldiphenylsiloxanes, such as the product DC 556 Cosmetic Grade Fluid from Dow Corning.

Silicone gums, in accordace with the invention, are polysiloxanes with a number-average molecular mass of between 200,000 and 5,000,000, used alone or as a mixture in a solvent. This solvent can be chosen from volatile silicones, polydimethylsiloxane (PDMS) oil, polyphenylmethylsiloxane (PPMS) oils, isoparaffins, polyisobutylenes, methylene chloride, pentane, dodecane, tridecanes or their mixtures.

Mention is made, for example, of the following compounds:
  polydimethylsiloxane,
  poly[(dimethylsiloxane)/(methylvinylsiloxane)],
  poly[(dimethylsiloxane)/(diphenylsiloxane)],
  poly[(dimethylsiloxane)/(phenylmethylsiloxane)], poly[(dimethylsiloxane)/(diphenylsiloxane)/(methylvinylsiloxane)].

Mention may be made, for example, of the following mixtures:

1) the mixtures formed from a polydimethylsiloxane hydroxylated at the chain end (Dimethiconol according to the CTFA nomenclature) and from a cyclic polydimethylsiloxane (Cyclomet cone according to the CTFA nomenclature), such as the product Q2 1401 sold by he company Dow Corning;
2) the mixtures formed from a polydimethylsiloxane gum with a cyclic silicone, such as the product SF 1214 Silicone Fluid from General Electric, which is an SE 30 gum with a molecular weight of 500,000 dissolved in SF 1202 Silicone Fluid (decamethylcyclopentasiloxane);
3) the mixtures of two polydimethylsiloxanes (PDMS) with different viscosities, in particular of a PDMS gum and of a PDMS oil, such as the products SF 1236 and CF 1241 from General Electric. The product SF 1236 is the mixture of an SE 30 oil defined above with a viscosity of 20 m$^2$/s and of an SF 96 oil with a viscosity of 5×10$^{-5}$ m$^2$/s (15% of SE 30 gum and 85% of SF 96 oil). The product CF 1241 is the mixture of an SE 30 gum (33%) and of a PDMS (67%) with a viscosity of 10$^{-3}$ m$^2$/s.

The silicone resins according to the invention are preferably crosslinked siloxane systems comprising the units: $R_2SiO_{2/2}$, $RSiO_{3/2}$ or $SiO_{4/2}$, in which R denotes a hydrocarbonaceous group having 1 to 6 carbon atoms or a phenyl group. The particularly preferred products among these are those where R denotes a lower ($C_1$–$C_4$)alkyl or phenyl radical.

Mention may be made, among these resins, of the product sold under the name Dow Corning 593 by Dow Corning or those sold under the name Silicone Fluid SS 4267 by General Electric, which are dimethyl/trimethylpolysiloxanes The polysiloxanes comprising, in their general structure, one or more organofunctional groups are in particular the polyalkylsiloxanes, polyarylsiloxanes or polyalkylarylsiloxanes as defined above comprising one or more organofunctional groups directly attached to the siloxane chain or attached via a hydrocarbonaceous radical.

The polysiloxanes with organofunctional groups of the invention can be selected from those comprising:

a) substituted or unsubstituted aminated groups, such as the products sold under the name GP 4 Silicone Fluid and GP 7100 by the company Genesee or the products sold under the names Q2 8220 and Dow Corning 929 or 939 by the company Dow Corning. The substituted aminated groups are in particular amino($C_1$–$C_4$)alkyl or amino($C_1$–$C_4$)alkylamino($C_1$–$C_4$)alkyl groups. Use is more particularly made of the silicones known as amodimethicone and trimethylsilylamodimethicone according to the CTFA name;
b) (per)fluorinated groups, such as trifluoroalkyl groups, such as, for example, those sold by Shin Etsu under the name FL 100;
c) thiol groups;
d) carboxylate groups, such as the products disclosed in European Patent EP 185,507, herein incorporated by reference, of Chisso Corporation;
e) hydroxylated groups, such as the polyorganopolysiloxanes with a hydroxy($C_2$–$C_{12}$)alkyl functional group disclosed in French Patent Application FR 85-16334, herein incorporate d by reference, and in particular the polyorganopolysiloxanes with a γ-hydroxypropyl functional group;
f) alkoxylated groups comprising at least 12 carbon atoms, such as the product Silicone Copolymer F755 from SWS Silicones and the products Abilwax® 2428, Abilwax® 2434 or Abilwax® 2440 from the company Goldschmidt;
g) acyloxyalkyl groups comprising at least 12 carbon atoms, such as the polyorganosiloxanes disclosed in French Patent Application FR 88-17433 and in particular the polydimethylsiloxanes with a stearoyloxypropyl functional group;
h) amphoteric groups, such as polydimethylsiloxanes with propylglycol betaine groups, such as the products Abil E200, B995, BC-1600 or BC-1602 from Goldschmidt, or with alkyl phosphobetaine groups, such as the products Pecosil SMQ-40 and SPB-1240 from Phoenix Chemical;
i) bisulphite groups;
j) hydroxyacylamino groups, such as the polydimethylsiloxanes with a hydroxyacylaminopropyl group disclosed in Application EP 342,834, herein incorporated by reference. Mention may be made, for example, of the product Q2-8413 from the company Dow Corning;
k) carboxylic acid groups or their salts, such as the products sold by BASF under the name Densodrin OF or by the company Wacker under the name MS 642 oil;
l) sulphonic groups;
m) sulphate or thiosulphate groups, such as polydimethylsiloxanes with a ω-thiosulphate groups, for example the products Abil S255, S32 and S201 from Goldschmidt.

The block copolymers having a linear polysiloxane-polyoxyalkylene block of (A—B)$_n$ type used in the context of the present invention preferably have the following general formula:

in which:

$R_2$ and $R_2'$, which are identical or different, represent a monovalent hydrocarbonaceous radical not comprising aliphatic unsaturation, n is an integer ranging from 2 to 4, a is an integer greater than or equal to 5, preferably of between 5 and 200 and more particularly still between 5 and 100, b is an integer greater than or equal to 4, preferably of between 4 and 200 and more particularly still between 5 and 100, c is an integer greater than or equal to 4, preferably of between 4 and 1000 and more particularly still between 5 and 300, Y represents a divalent organic group which is bonded to the adjacent silicon atom by a carbon-silicon bond and to polyoxyalkylene block by an oxygen atom, the average molecular weight of each siloxane block is between approximately 400 and approximately 10,000, that of each polyoxyalkylene block being between approximately 300 and approximately 10,000, the siloxane blocks represent from approximately 10% to approximately 95% by weight of the block copolymer, the weight-average molecular weight of the block copolymer being at least 3000 and preferably between 5000 and 1,000,000 and more particularly still between 10,000 and 200,000.

$R_2$ and $R_2'$ are preferably chosen from the group comprising alkyl radicals, such as, for example, the methyl, ethyl, propyl, butyl, pentyl, hexyl, octyl, decyl or dodecyl radicals, aryl radicals, such as, for example, phenyl or naphthyl, aralkyl radicals, such as, for example, benzyl or phenylethyl, and tolyl, xylyl and cyclohexyl radicals.

Y is preferably —R"—, —R"—CO—, —R"—NHCO—, —R"—NH—CO—NH—R'"—NHCO— or —R"—OCONH—R'"—NHCO—, where R" is a divalent alkylene group, such as, for example, ethylene, propylene or butylene, and R'" is a divalent alkylene group or a divalent arylene group, such as —$C_6H_4$—, —$C_6H_4$—$C_6H_4$—, —$C_6H_4$—$CH_2$—$C_6H_4$— or —$C_6H_4$—$C(CH_3)_2$—$C_6H_4$—.

More preferably still, Y represents a divalent alkylene radical, more particularly the —$CH_2$-$CH_2$-$CH_2$— radical or the $C_4H_8$ radical.

The preparation of the block copolymers employed in the context of the present invention is disclosed in European Application EP 0,492,657 A1, the teaching of which is incorporated reference in the present description.

The polymers with a non-silicone organic backbone grafted with monomers comprising a polysiloxane, in accordance with the invention, are chosen more preferably from those disclosed in Patents U.S. Pat. No. 4,693,935, U.S. Pat. No. 4,728,571 and U.S. Pat. No. 4,972,037 and Patent Applications EP-A-0,412,704, EP-A-0,412,707, EP-A-0, 640,105 and WO 95/00578, the teachings of which are entirely incorporated by reference into the present description. They are copolymers obtained by radical polymerization from monomers with ethylenic unsaturation and from silicone macromers having an end vinyl group or else copolymers obtained by reaction of a polyolefin comprising functionalized groups and of a polysiloxane macromer having an end functional group which reacts with the said functionalized groups.

Examples of polymers with a polysiloxane backbone grafted with non-silicone organic monomers which are suitable for the implementation of the present invention, and their specific method of preparation, are disclosed in particular in Patent Applications EP-A-0,582,152, WO 93/23009 and WO 95/03776, the teachings of which are entirely incorporated by reference into the present description.

According to the invention, all the silicones can also be used in the form of emulsions or of microemulsions. The silicones which are particularly preferred in accordance with the invention are:

polydimethylsiloxanes with end trimethylsilyl groups, such as oils having a viscosity of between 0.2 and 2.5 $m^2/s$ at 25° C., such as the oils of the DC200 series from Dow Corning, in particular that with a viscosity of 60,000 cSt, oils of the Silbione® 70047 and 47 series and more particularly Silbione® 70 047 V 500 000 oil, which are sold by the company Rhoda Chimie, i)r the silicone oil AK 300,000 from the company Wacker, polydimethylsiloxanes with end dimethylsilanol groups, such as dimethiconols;

polysiloxanes with aminated groups, such as amodimethicones or trimethylsilylamodimethicones.

According to the invention, the silicone or silicones can represent from 0.001% to 10% by weight, preferably from 0.005% to 5% by weight and more preferably still from 0.01% to 3% y weight of the total weight of the final composition.

The compositions of the invention, in addition, advantageously comprise at least one other surface-active agent which is generally present in an amount of between 0.1% and 40% by weight approximately, preferably between 3% and 30% and more preferably still between 5% and 20% with respect to the total weight of the composition.

This surface-active agent can be chosen from anionic, amphoteric, non-ionic or cationic surface-active agents or their mixtures.

The additional surfactants which are suitable for implementing the present invention are in particular the following:

(i) Anionic Surfactant(s):

Their nature does not generally assume a critical character within the context of the present invention.

Thus, by way of example of anionic surfactants that can be used, alone or as mixtures, in the context of the present invention, there may be mentioned in particular (non-limiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylarylpolyether sulphates, monoglyceride sulphates; alkylsulphonates, alkyl phosphates, alkylamidesulphonates, alkylarylsulphonates, α-olefinsulphonates, paraffinsulphonates; alkyl sulphosuccinates, alkyl ether sulphosuccinates, alkylamidesulphosuccinates; alkyl sulphosuccinamates; alkyl sulphoacetates; alkyl ether phosphates; acylsarcosinates; acylisethionates and N-acyltaurates, the alkyl or acyl radical of all these different compounds preferably comprising from 8 to 24 carbon toms, and the aryl radical preferably denoting a phenyl or benzyl group. Among he anionic surfactants which are further usable, there may also be mentioned the salts of fatty acids, such as the salts of oleic, ricinoleic, palmitic and stearic acids, the acids of copra oil or of hydrogenated copra oil, and acyllactylates in which the acyl radical comprises 8 to 20 carbon atoms. It is also possible to use weakly anionic surfactants, like alkyl-D-galactosideuronic acids and salts thereof, as well as the olyoxyalkylenated ($C_6$–$C_{24}$)alkyl ether carboxylic acids, the polyoxyalkylenated ($C_6$–$C_{24}$)alkylaryl ether carboxylic acids, the polyoxyalkylenated ($C_6$–$C_{24}$)alkylamido ether carboxylic acids and salts thereof, in particular those comprising from to 50 ethylene oxide groups, and mixtures thereof.

Among the anionic surfactants, it is preferable to use, according to the invention, alkyl sulphate and alkyl ether sulphate salts and mixtures thereof.

(ii) Non-ionic Surfactant(s):

The non-ionic surface-active agents themselves are also compounds which are well known per se (in this resect see in particular the "Handbook of Surfactants" by M. R. Porter, published by Blackie & Son (Glasgow and London), 1991, pp. 116–178) and, in the context of the present invention, their nature does not generally assume any critical character. They can thus be chosen especially from (non-limiting list) fatty alcohols, alpha-diols, alkylphenols or acids which are polyethoxylated, polypropoxylate or polyglycerolated, having a fatty chain comprising, for example, 8 to 18 carbon atoms, it being possible for the number of ethylene oxide or propylene oxide groups to range especially from 2 to 50 and it being possible for the number of glycerol groups to range especially from 2 to 30. Mention may also be made of the copolymers of ethylene and propylene oxide and the condensates of ethylene and propylene oxide with fatty alcohols; the polyethoxylated fatty amides preferably having from 2 to 30 mol of ethylene oxide, the polyglycerolated fatty amide on average comprising 1 to 5 glycerol groups and in particular 1.5 to 4; the polyethoxylated fatty amines preferably having 2 to 30 mol of ethylene oxide; the oxyethylenated esters of sorbitan fatty acids having from 2 to 30 mol of ethylene oxide; the sucrose esters of fatty acids, the polyethylene glycol esters of fatty acids, alkylpolyglycosides, the N-alkylglucamine derivatives, or amine oxides, such as the oxides of $(C_{10}-C_{14})$alkylamines or the N-acylamino-propylmorpholine oxides. It will be noted that alkylpolyglycosides constitute non-ionic surfactants which enter particularly well into the scope of the present invention.

(iii) Amphoteric Surfactant(s):

The additional amphoteric surface-active agents, the nature of which does not assume any critical character in the context of the present invention, may be especially (non-limiting list) derivatives of aliphatic secondary or tertiary amines in which the aliphatic radical is a linear or branched chain comprising 8 to 22 carbon atoms and comprising at least one water-solubilizing anionic group (for example carboxylate, sulphonate, sulphate, phosphate or phosphonate); $(C_8-C_{20})$alkyl betaines, sulphobetaines, $(C_8-C_{20})$alkyl amido$(C_1-C_6)$alkyl betaines or $(C_8-C_{20})$alkylamido$(C_1-C_6)$alkyl sulphobetains may further be mentioned.

Among the amine derivatives, there may be mentioned products sold under the name Miranol, as described in Patents U.S. Pat. No. 2,528,378 and U.S. Pat. No. 2,781,354, both of which are incorporated by reference, and with structures:

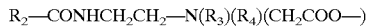

in which $R_2$ denotes an alkyl radical derived from an acid $R_2$—COOH present in hydrolysed coconut oil, for example, a saturated or unsaturated, linear or branched $(C_5-C_{19})$alkyl radical, a heptyl, nonyl or undecyl radical, $R_3$ denotes a beta-hydroxyethyl group and $R_4$ a carboxymethyl group; and

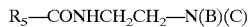

in which B represents —$CH_2CH_2OX'$, C represents —$(CH_2)_z$—Y', with z=1 or 2, X' denotes the —$CH_2CH_2$—COOH group or a hydrogen atom, Y' denotes —COOH or the radical —$CH_2$—CHOH—$SO_3H$, $R_5$ denotes an alkyl radical of a carboxylic acid present in coconut oil or in hydrosed linseed oil, for example, a saturated or unsaturated, linear or branched $(C_5-C_{19})$alkyl radical, an alkyl radical, in particular $C_7$, $C_9$, $C_{11}$ or $C_{13}$, a $C_{17}$ alkyl radial and its iso form or an unsaturated radical $C_{17}$.

These compounds are classified in the CTFA dictionary, 7th Edition, 1997, under the names Disodium Cocomphodiacetate, Disodium Lauroamphodiacetate, Disodium Capryloamphodiacetat , Disodium Caproamphodiacetate, Disodium Cocoamphodipropionate, Disodium Lauroamphodipropionate, Disodium Caproamphodipropionate, Disodium Capryloamphodipropionate, Lauroamphodipropionic acid and Cocoamphodipropionic acid. By way of example, there may be mentioned disodium cocoamphodiacetate sold under the trade name Miranol® C2M concentrated by the company Rhodia Chimie.

In the compositions in accordance with the invention, use is preferably made of mixtures of surface-active agents and in particular mixtures of anionic surface active agents or mixtures of anionic surface-active agents and of amphoteric or non-ionic surface-active agents.

Use is preferably made, as at least one additional anionic surface-active agent, of sodium, triethanolaminie, or ammonium $(C_{12}-C_{14})$alkyl sulphates, sodium, triethanolamine or ammonium $(C_{12}-C_{14})$alkyl ether sulphates oxyethylenated with 2.2 mol of ethylene oxide, sodium cocoylisethionate and sodium alpha-$(C_{14}-C_{16})$olefinsulphonate and mixtures thereof with:

either an amphoteric surface-active agent, such as the amine derivatives named disodium cocoamphodipropionate or sodium cocoamphopropionate sold in particular by the company Rhodia Chimie under the trade name "Miranol® C2M Conc" as an aqueous solution comprising 38% of active material or under the name Miranol® C32;

or an amphoteric surface active agent, such as alkyl betaines, in particular the coco betaine sold under the name "Dehyton® AB 30" as an aqueous solution comprising 32% of AM by the company Henkel, or such as $(C_8-C_{20})$alkyl amido$(C_1-C_6)$alkyl betaines, in particular Tegobetaine® F 50 sold by the company Goldschmidt.

Use may also be made of at least one cationic surfactant, among which may be mentioned in particular (non-limiting list): the salts of optionally polyoxyalkylenated primary, secondary or tertiary fatty amines; quaternary ammonium salts, such as tetraalkyammonium, alkylamidoalkyltrialkylammonium, trialkylbenzylammonium, trialkyl hydroxyalkylammonium or alkylpyridinium chlorides or bromides; imidazoline derivatives; or amine oxides of cationic nature.

The at least one anionic surface-active agent, other than the 2-hydroxyalkyl ether carboxylic acid or salts the is generally present in a proportion of 1 to 30% by weight, preferably of 3 t 15% by weight, with respect to the total weight of the composition.

The at least one amphoteric or non-ionic surface-active agent is generally present in a proportion of 0.5 to approximately 15% by weight, preferably of 1 to 5% by weight, with respect to the total weight of the composition.

The amounts and the qualities of the surfactants are those sufficient to confer a satisfactory foaming and/or detergent power on the final composition.

In the composition according to the present invention, the combined detergent surfactants generally represent from 4 to 50% by weight and preferably from 6 to 35% by weight and more particularly from 8 to 25% by weight with respect to the total weight of the composition.

The composition of the invention can also comprise at least one additive chosen from thickeners, fragrances pearlescent agents, preservatives, sunscreens, anionic or non-ionic or amphoteric polymers, cationic polymers, proteins, protein hydrolysates, ceramides, pseud ceramides, fatty acids with linear or branched $C_{16}-C_{40}$ chains, such as 18-methyleicosanoic acid, hydroxy acids, vitamins, panthenol, vegetable oils, miner oils and synthetic oils, antidandruff agents and any other additive conventionally used in the cosmetics field which does not affect the stability and the properties of the compositions according to the invention.

These additives are present in the composition according to the invention in proportions which can range from 0 to 50% by weight with respect to the total weight of the composition. The precise amount of each additive is easily determined by a person skilled in the art according to its nature and function.

According to a preferred form of the invention, the compositions according to the invention additionally comprise one or more cationic polymers.

The cationic polymers which can be used in accordance with the present invention can be chosen from all those already known per se as improving the cosmetic properties of hair treat detergent compositions, namely, in particular, those disclosed in Patent Application EP-A-0,337,354 and in French Patent Applications FR-A-2,270,846, 2,383,660, 2,598,611, 2,470,596 and 2,519,863, all of which are incorporated herein by reference.

More generally still, within the meaning of the present invention, the expression "cationic polymer" denotes any polymer comprising cationic groups and/or groups which can be ionized to cationic groups.

Preference is given, among all the cationic polymers which can be used in the context of the present invention, to the use of quaternary derivatives of cellulose ether, such as the products sold under the name "JR 400" by the company Union Carbide Corporation, cyclopolymers, in particular diallyidimethylammonium salt homopolymers and copolymers of diallyidimethylammonium salt and of acrylamide, in particular the chlorides, sold under the names "Merquat 100", "Merquat 550" and "Merquat S" by the company Merck, or cationic polysaccharides and more particularly guar gums modified by 2,3-epoxypropyltrimethylammonium chloride, sold, for example, under the name "Jaguar C13S" by the company Meyhall.

Use may also be made of polymers which are composed of repeat units corresponding to the formula:

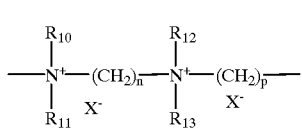

(V)

in which $R_{10}$, $R_{11}$, $R_{12}$ and $R_{13}$, which are identical or different, denote an alkyl or hydroxyalkyl radical having from 1 to 4 carbon atoms approximately, n and p are integers varying from 2 to 20 approximately and $X^-$ is an anion derived from an inorganic or organic acid.

According to the invention, the cationic polymer or polymers can represent from 0.001% to 10% by weight, preferably from 0.005% to 5% by weight and more preferably still from 0.01% to 3% by weight of the total weight of the final composition.

The cosmetically acceptable medium can be composed solely of water or of a mixture of water and of a cosmetically acceptable solvent, such as a lower $C_1$–$C_4$ alcohol, for example ethanol, isopropanol, tert-butanol or n-butanol, alkylene glycols, for example propylene glycol, or glycol ethers.

The composition preferably comprises from 50 to 95% by weight of water with respect to the total weight of the composition.

The detergent compositions according to the invention exhibit a final pH generally of between 3 and 10. This pH is preferably between 4 and 8. The pH can be conventionally adjusted to the desired value by addition of a base (organic or inorganic) to the composition, for example aqueous ammonia or a primary, secondary or tertiary (poly)amine, such as monoethanolamine, diethanolamine, triethanolamine, isopropanolamine or 1,3-propanediamine, or alternatively by addition of an acid, preferably a carboxylic acid, such as, for example, citric acid.

The compositions in accordance with the invention can comprise, in addition to the combination defined above, viscosity-regulating agents, such as electrolytes, or thickening agents. Mention may in particular be made of sodium chloride, scleroglucans, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked poly(acrylic acid)s and crosslinked acrylic acid/$C_{10}$–$C_{30}$ alkyl acrylate copolymers. These viscosity-regulating agents are used in the compositions according to the invention in proportions which can range up to 10% by weight with respect to the total weight of the composition.

The compositions in accordance with the invention can also comprise up to 5% of pearlescent or opacifying agents well known in the state of the art, such as, for example, sodium or magnesium palmitates, sodium or magnesium stearates and hydroxystearates, acylated derivatives with a fatty chain, such as ethylene glycol or polyethylene glycol monostearates or distearates, or ethers with fatty a chains, such as, for example, distearyl ether or 1-(hexadecyloxy)-2-octadecanol.

The compositions according to the invention can also comprise foam synergists, such as $C_{10}$–$C_{18}$ 1,2-alkanediols or fatty alkanolamides derived from mono- or from diethanolamine.

The compositions in accordance with the invention can be used for washing and treating keratinous substances, such as the hair, skin, eyelashes, eyebrows, nails, lips or scalp and more particularly the hair.

In particular, the detergent compositions according to the invention are shampoos, shower gels and foam baths.

The compositions of the invention can also be provided in the form of a rinse-out or leave-in conditioner or of perming, hair-straightening, dyeing or bleaching compositions or in the form of rinse-out compositions, to be applied before or after a dyeing, bleaching, perming or hair straightening or between the two stages of a perming or hair straightening.

The compositions of the invention can also be provided in the form of make-up removers.

The compositions according to the invention can be provided in the form of a gel, milk, cream, emulsion, thickened lotion or foam and can be used for the skin, scalp, nails, eyelashes, lips and more particularly the hair.

These detergent compositions are preferably foaming and the foaming power of the compositions according to the invention, characterized by a foam height, is generally greater than 75 mm, preferably greater than 100 mm, measured according to the modified Ross-Miles method (NF T 73-404/ISO696). The modifications to the method are as follows:

The measurement is carried out at a temperature of 22° C. with water purified by osmosis. The concentration f the solution is 2 g/l. The height of the drop is 1 m. The amount of composition which drops is 200 ml. These 200 ml of composition fall into a measuring cylinder having a diameter of 50 mm and comprising 50 ml of the composition to be tested. The measurement is made 5 minutes after the composition has finished being un in.

A further subject-matter of the invention is a process for the treatment of keratinous substances, such as the skin or hair, characterized in that it consists in applying, to the keratinous substances, a cosmetic composition as defined above and in then optionally rinsing, in particular with water.

This process according to the invention thus makes it possible to treat, care for, wash or remove make-up from the skin, hair or any other keratinous substance.

In everything which follows or precedes, the percentages expressed are by weight.

The invention will now be more fully illustrated using the following examples, which should not be regarded as limiting it to the embodiments described. In the examples, AM means active material.

EXAMPLE 1

Two shampoo compositions were prepared, one in accordance with the invention (composition A) and the other comparative (composition B):

| | A (Invention) | B |
|---|---|---|
| Sodium 2-(2-hydroxylauryloxy acetate as an aqueous solution with an active material content of 30% (Beaulight Shaa from Sanyo) | 10 g AM | — |
| Sodium ($C_{12}$–$C_{14}$) alkyl ether sulphate oxyethylenated with 2.2 mol of ethylene oxide as an aqueous solution with an AM content of 70% | 5 g AM | 5 g AM |
| Sodium lauryl ether carboxylate with 4.5 EO as an aqueous solution with an active material content of 22% (Akyposoft 45 NV from Kao) | — | 10 g AM |
| Polydimethylsiloxane as a non-ionic aqueous emulsion with an AM content of 50% (DC2-1691 from Dow Corning) | 2.5 g AM | 2.5 g AM |
| Ether of myristyl glycol and of cetearyl alcohol oxyethylenated with 60 mol of ethylene oxide (Elfacos GT 282S from Akzo) | 1 g | 1 g |
| Preservatives | q.s. | q.s. |
| pH | 6.6 | 6.6 |
| Demineralized water, q.s. for | 100 g | 100 g |

Shampooing was carried out by applying approximately 1 g of the composition A to 2.5 g locks of leached hair (SA20) which had been wetted beforehand. The shampoo was made to foam, left to stand for 10 minutes and was then rinsed copiously with water. The locks were dried for 10 minutes at 60° C. The same procedure as above was tarried out with the comparative composition B.

A panel of experts evaluated the appearance of the dried hair. The object of the test used was the grading, by a jury, of each series of 2 samples by attributing the grade 1 to the lock which showed the better disentangling, which ass the softer and which was the sleeker, and 2 to the other. The 2 locks of the same series were presented simultaneously to the judge. Statistical analysis of the results was carried out using the tables of A. Kramer (Food Technology, 17(12), 124–125, 1963).

All the experts indicated that the hair treated with the composition A according to the invention was significantly softer and sleeker and more easily disentangled than that treated with the composition B.

EXAMPLE 2

Two shampoo compositions were prepared, one in accordance with the invention (composition A) and the other comparative (composition B):

| | A (Invention) | B |
|---|---|---|
| Sodium 2-(2-hydroxylauryloxy) acetate as an aqueous solution with an AM content of 30% (Beaulight Shaa from Sanyo) | 10 g AM | — |
| Sodium ($C_{12}$–$C_{14}$) alkyl ether sulphate oxyethylenated with 2.2 mol of ethylene oxide as an aqueous solution with an AM content of 70% | 4 g AM | 14 g AM |
| Hexadimethrine chloride as an aqueous solution with an AM content of 60% (Mexomer PO from Chimex | 0.6 g AM | 0.6 g AM |
| Polydimethylsiloxane as a non-ionic aqueous emulsion with an AM content of 50% (DC2-1691 from Dow Corning) | 2.5 g AM | 2.5 g AM |
| Xanthan gum (Keltrol T from Nutrasweet Kelco) | 1 g | 1 g |
| Preservatives | q.s. | q.s. |
| Demineralized water, q.s. for | 100 g | 100 g |

Shampooing was carried out by applying approximately 1 g of the composition A to 2.5 g locks of bleached hair (SA20) which had been wetted beforehand. The shampoo was made to foam, left to stand for 10 minutes and was then rinsed copiously with water. The locks were dried for 10 minutes at 60° C. The same procedure as above was carried out with the comparative composition B.

A panel of experts evaluated the appearance of the dried hair. All the experts indicated that the hair treated with the composition A according to the invention was significantly softer and more easily disentangled than that treated with the composition B.

EXAMPLE 3

A shampoo composition in accordance with the invention was prepared:

| | |
|---|---|
| Sodium 2-(2-hydroxylauryloxy) acetate in aqueous solution with an active material (AM) content of 30% (Beaulight Shaa from Sanyo) | 5 g AM |
| Sodium ($C_{12}$–$C_{14}$) alkyl ether sulphate oxyethylenated with 2.2 mol of ethylene oxide as an aqueous solution with an AM content of 70% | 15 g AM |
| Cocoyl betaine as an aqueous solution with an AM content of 30% | 5 g AM |
| Polydimethylsiloxane with a viscosity of 300,000 cSt | 1.5 g |
| Xanthan gum (Keltrol T from Nutrasweet Kelco) | 1 g |
| Preservatives | q.s. |
| Demineralized water, q.s. for | 100 g |

The hair treated with the composition according to the invention is soft and sleek and easily disentangled.

What is claimed is:

1. A detergent cosmetic composition comprising at least one anionic surfactant chosen from 2-hydroxyalkyl ether carboxylic acid and salts thereof, and at least one silicone polymer chosen from:
   (i) volatile or non-volatile, linear, branched or cyclic and crosslinked or non-crosslinked polyalkylsiloxanes, polyarylsiloxanes or polyalkylarylsiloxanes;
   (ii) polysiloxanes comprising, in their general structure, at least one organofunctional group chosen from:
      a) substituted or unsubstituted aminated groups;
      b) (per)fluorinated groups;
      c) thiol groups;
      d) carboxylate groups;
      e) hydroxylated groups;
      f) alkoxylated groups;
      g) acyloxyalkyl groups;
      h) amphoteric groups;
      i) bisulphite groups;
      j) hydroxyacylamino groups;

k) carboxylic acid groups;
l) sulphonic groups; and
m) sulphate or thiosulphate groups;
(iii) linear polysiloxane(A)-polyoxyalkylene(B) block copolymers having the general structure $(A-B)_n$ with $n>3$;
(iv) grafted silicone polymers with a non-silicone organic backbone, which polymers are composed of a main organic chain formed from organic monomers not comprising silicone, on which chain is grafted, inside the said chain and optionally at one at least of its ends, at least one polysiloxane macromonomer; and
(v) grafted silicone polymers with a polysiloxane backbone which is grafted with non-silicone organic monomers, comprising a main polysiloxane chain on which is grafted, inside the said chain and optionally at one at least of its ends, at least one organic macromonomer not comprising silicone.

2. A composition according to claim 1, wherein said at least one anionic surfactant has the following structure:

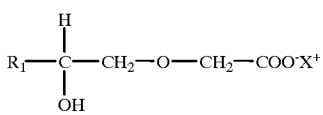

(I)

wherein
$R_1$ denotes a saturated or unsaturated, linear or branched alkyl radical comprising from 8 to 30 carbon atoms; and
X denotes hydrogen or an inorganic or organic cation.

3. A composition according to claim 2, wherein said $R_1$ radical denotes a saturated or unsaturated, linear or branched alkyl radical comprising from 8 to 18 carbon atoms.

4. A composition according to claim 2, wherein said $R_1$ radical is a radical derived from coconut oil.

5. A composition according to claim 1, wherein said at least one silicone polymer is in the form of an oil, a wax, a resin, or a gum.

6. A composition according to claim 1, wherein said at least one silicone polymer is chosen from polydimethylsiloxanes with at least one end trimethylsilyl group; polydimethylsiloxanes with at least one end dimethylsilanol group; and polysiloxanes with at least one aminated group.

7. A composition according to claim 6, wherein said at least one end dimethylsilyl group is chosen from dimethiconols.

8. A composition according to claim 6, wherein said at least one aminated group is chosen from amodimethicone end groups and trimethylsilylamodimethicone end groups.

9. A composition according to claim 1, wherein said at least one anionic surfactant is present in a concentration ranging from 1 and 30% by weight with respect to the total weight of the composition.

10. A composition according to claim 1, wherein said at least one anionic surfactant is present in a concentration ranging from 3 and 15% by weight with respect to the total weight of the composition.

11. A composition according claim 1, wherein said at least one silicone polymer is present in a concentration ranging from 0.001% and 10% by weight with respect to the total weight of the composition.

12. A composition according claim 1, wherein said at least one silicone polymer is present in a concentration ranging from 0.005% and 5% by weight with respect to the total weight of the composition.

13. A composition according claim 1, wherein said at least one silicone polymer is present in a concentration ranging from 0.01% and 3% by weight with respect to the total weight of the composition.

14. A composition according to claim 1, further comprising at least one additional surface-active agent chosen from at least one anionic surfactant, at least one cationic surfactant, at least one non-ionic surfactant, and at least one amphoteric surfactant.

15. A composition according to claim 14, wherein said at least one additional surface-active agent is present in a concentration ranging from 0.5% and 40% by weight with respect to the total weight of the composition.

16. A composition according to claim 14, wherein said at least one additional surface-active agent is present in a concentration ranging from 3% and 30% by weight with respect to the total weight of the composition.

17. A composition according to claim 14, wherein said at least one additional surface-active agent is present in a concentration ranging from 5% and 20% by weight with respect to the total weight of the composition.

18. A composition according to claim 1, further comprising at least one additive chosen from thickeners fragrances, pearlescent agents, preservatives, sunscreens, anionic or non-ionic or amphoteric polymers, cationic polymers, proteins, protein hydrolysates, ceramides, pseudoceramides, a fatty acid with linear or branched $C_{16}$–$C_{40}$ chains, hydroxy acids, vitamins, panthenol, vegetable oils, mineral oils, synthetic oils and a antidandruff agents.

19. A composition according to claim 18, wherein said fatty acid with linear or branched $C_{16}$–$C_{40}$ chain is 18-methyleicosanoic acid.

20. A composition according to claim 18, wherein said cationic polymers are chosen from:
diallyidimethylammonium salt homopolymers and copolymers of diallyidimethylammonium salt an of acrylamide;
quaternary derivatives of cellulose ether;
cationic polysaccharides;
polymers which are composed of repeat units corresponding to the formula:

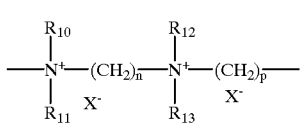

(V)

in which $R_{10}$, $R_{11}$, $R_{12}$ and $R_{13}$, which are identical or different, denote an alkyl or hydroxyalkyl radical having from 1 to 4 carbon atoms, n and p are integers varying from 2 to 20 and $X^-$ is an anion derived from an inorganic or organic acid; and
mixtures thereof.

21. A composition according to claim 1, wherein said composition is in a cosmetically acceptable aqueous medium.

22. A composition according to claim 1, wherein said composition is in the form of a shampoo, a composition for washing the skin, a rinse-out or leave-in conditioner, permanent-waving the hair, a composition for straightening the hair, a composition for dyeing the hair, or a composition for bleaching the hair.

23. A composition according to claim 1, wherein said composition is in the form of a rinse-out composition be applied before or after dyeing, bleaching, permanent-waving or straightening the hair, or between the two steps of a permanent-waving or hair-straightening operation.

24. A process for washing keratin substances comprising applying to said keratin substances a cosmetic composition comprising at least one anionic surfactant chosen from 2-hydroxyalkyl ether carboxylic acid and salts thereof, and at least one silicone polymer chosen from:
  (i) volatile or non-volatile, linear, branched or cyclic and crosslinked or non-crosslinked polyalkylsiloxanes, polyarylsiloxanes or polyalkylarylsiloxanes;
  (ii) polysiloxanes comprising their general structure, at least one organofunctional group chosen from:
    a) substituted or unsubstituted aminated groups;
    b) (per)fluorinated groups;
    c) thiol groups;
    d) carboxylate groups;
    e) hydroxylated groups;
    f) alkoxylated groups;
    g) acyloxyalkyl groups;
    h) amphoteric groups;
    i) bisulphite groups;
    j) hydroxyacylamino groups;
    k) carboxylic acid groups;
    l) sulphonic groups; and
    m) sulphate or thiosulphate groups;
  (iii) linear polysiloxane(A)-polyoxyalkylene(B) block copolymers having the general structure $(A-B)_n$ with n>3;
  (iv) grafted silicone polymers with a non-silicone organic backbone, which polymers are composed of a main organic chain formed from organic monomers not comprising silicone, on which chain is grafted, inside the said chain and optionally at one at least of its ends, at least one polysiloxane macromonomer; and
  (v) grafted silicone polymers with a polysiloxane backbone which is grafted with non-silicone organic monomers, comprising a main polysiloxane chain on which is grafted, inside the said chain and optionally at one at least of its ends, at least one organic macromonomer not comprising silicone, and rinsing said washed keratin substances.

25. A process according to claim 24, wherein said keratin substances are hair.

26. A process for disentangling or sleeking hair or for contributing volume, lightness, softness, suppleness and manageability to hair comprising applying to said hair a composition comprising at least one anionic surfactant chosen from 2-hydroxyalkyl ether carboxylic acid and salts thereof, and at least one silicone polymer chosen from:
  (i) volatile or non-volatile, linear, branched or cyclic and crosslinked or non-crosslinked polyalkylsiloxanes, polyarylsiloxanes or polyalkylarylsiloxanes;
  (ii) polysiloxanes comprising in their general structure, at least one organofunctional group chosen from:
    a) substituted or unsubstituted aminated groups;
    b) (per)fluorinated groups;
    c) thiol groups;
    d) carboxylate groups;
    e) hydroxylated groups;
    f) alkoxylated groups;
    g) acyloxyalkyl groups;
    h) amphoteric groups;
    i) bisulphite groups;
    j) hydroxyacylamino groups;
    k) carboxylic acid groups;
    l) sulphonic groups; and
    m) sulphate or thiosulphate groups;
  (iii) linear polysiloxane(A)-polyoxyalkylene(B) block copolymers having the general structure $(A-B)_n$ with n>3;
  (iv) grafted silicone polymers with a non-silicone organic backbone, which polymers are composed of a main organic chain formed from organic monomers not comprising silicone, on which chain is grafted, inside the said chain and optionally at one at least of its ends, at least one polysiloxane macromonomer; and
  (v) grafted silicone polymers with a polysiloxane backbone which is grafted with non-silicone organic monomers, comprising a main polysiloxane chain on which is grafted, inside the said chain and optionally at one at least of its ends, at least one organic macromonomer not comprising silicone.

27. A process for the treatment of keratinous substances comprising applying to said keratinous substances a composition applying to said keratin substances a cosmetic composition comprising at least one anionic surfactant chosen from 2-hydroxyalkyl ether carboxylic acid and salts thereof, and at least one silicone polymer chosen from:
  (i) volatile or non-volatile, linear, branched or cyclic and crosslinked or non-crosslinked polyalkylsiloxanes, polyarylsiloxanes or polyalkylarylsiloxanes;
  (ii) polysiloxanes comprising in their general structure, at least one organofunctional group chosen from:
    a) substituted or unsubstituted aminated groups;
    b) (per)fluorinated groups;
    c) thiol groups;
    d) carboxylate groups;
    e) hydroxylated groups;
    f) alkoxylated groups;
    g) acyloxyalkyl group ;
    h) amphoteric groups;
    i) bisulphite groups;
    j) hydroxyacylamino groups;
    k) carboxylic acid groups;
    l) sulphonic groups; and
    m) sulphate or thiosulphate groups;
  (iii) linear polysiloxane(A)-polyoxyalkylene(B) block copolymers having the general structure $(A-B)_n$ with n>3;
  (iv) grafted silicone polymers with a non-silicone organic backbone, which polymers are composed of a main organic chain formed from organic monomers not comprising silicone, on which chain is grafted, inside the said chain and optionally at one at least of its ends, at least one polysiloxane macromonomer; and
  (v) grafted silicone polymer with a polysiloxane backbone which is grafted with non-silicone organic monomers, comprising a main polysiloxane chain on which is grafted, inside the said chain and optionally at one at least of its ends, at least one organic macromonomer not comprising silicone.

28. A process according to claim 27, wherein said keratin substances are hair.

29. A process according to claim 27, further comprising rinsing said treated keratin substances.

* * * * *

UNITED STATES PATENT AND TRADEMARK OFFICE
CERTIFICATE OF CORRECTION

PATENT NO. : 6,368,584 B1
DATED : April 9, 2002
INVENTOR(S) : Nathalie Garnier et al.

It is certified that error appears in the above-identified patent and that said Letters Patent is hereby corrected as shown below:

Column 15,
Lines 60 and 64, "according claim" should read -- according to claim --.

Column 16,
Line 1, "according claim" should read -- according to claim --.
Line 23, "thickeners fragrances" should read -- thickeners, fragrances --.
Line 29, before "antidandruff", delete "a".
Lines 35 and 36, "diallyidimethylammonium" should read
-- diallyldimethylammonium --.
Line 36, "an" should read -- and --.
Line 66, "composition be" should read -- composition to be --.

Column 17,
Line 11, "comprising their" should read -- comprising, in their --.
Line 54, "comprising in" should read -- comprising, in --.

Column 18,
Line 5, "$(A-B)_n$ with" should read -- $(A-B)_n$ with --.
Line 30, "comprising in" should read -- comprising, in --.
Line 38, "group;" should read -- groups; --.

Signed and Sealed this

Twenty-ninth Day of October, 2002

*Attest:*

JAMES E. ROGAN
*Attesting Officer*  *Director of the United States Patent and Trademark Office*